United States Patent [19]

Nappholz

[11] Patent Number: 5,792,198
[45] Date of Patent: Aug. 11, 1998

[54] AUTO ADAPTATION OF RR INTERVAL IN IMPLANTABLE PACEMAKER

[76] Inventor: Tibor A. Nappholz, 8524 E. Jamison Ave., Englewood, Colo. 80112

[21] Appl. No.: 839,926

[22] Filed: Apr. 21, 1997

Related U.S. Application Data

[60] Provisional application No. 60/016,552 Apr. 30, 1996.
[51] Int. Cl.⁶ .................................................. A61N 1/365
[52] U.S. Cl. .................................................. 607/18
[58] Field of Search .................................. 607/9, 17, 18, 607/19

[56] References Cited

U.S. PATENT DOCUMENTS

| | | |
|---|---|---|
| 4,856,522 | 8/1989 | Hansen . |
| 5,487,753 | 1/1996 | MacCarter et al. ............ 607/17 |

*Primary Examiner*—Scott M. Getzow
*Attorney, Agent, or Firm*—Gottlieb, Rackman & Reisman

[57] ABSTRACT

In an implantable rate responsive pacemaker a metabolic demand parameter is mapped in accordance with a rate response function into a corresponding metabolic indicated rate for pacing a patient's heart. In addition, a physical fitness monitor is also provided which monitors the patient's physical fitness and generates a long term true and accurate physical indicia. This indicia is used to adjust the rate response function so that it is automatically adjusted to the physical fitness of the patient.

18 Claims, 6 Drawing Sheets

AUTO ADAPTATION OF RR INTERVAL IN IMPLANTABLE PACEMAKER

This application claims the benefits of U.S. Provisional Application No. 60/016,552, filed Apr. 30, 1996.

BACKGROUND OF THE INVENTION

A. Field of Invention

This invention pertains to implantable pacemakers, and more particularly, to a pacemaker which self-adjusts one or more of its pacing parameters in accordance with the long-term physical fitness of the patient.

B. Description of the Prior Art

Initially, pacemakers were simply pulse generators which generated and delivered to a patient cardiac stimulation pulses at predetermined intervals independent of any intrinsic cardiac activity. Next, pacemakers were made which sensed intrinsic cardiac activity and allowed a cardiac stimulation pulse to be delivered only in the absence of intrinsic cardiac activity during a certain time window. These pacemakers are normally referred to as 'demand pacemakers'.

The next major step in pacemaker technology was the rate responsive pacemakers. These pacemakers not only sensed intrinsic cardiac activity to deliver pacing pulses on demand but also sensed the current metabolic demand of the patient and adjusted the pacing intervals accordingly. This mode of operation is prevalent in most implantable pacemakers available today. The metabolic demand is determined either by measuring a physiological parameter related to the operation of the heart, such as the minute volume, the QT interval or the depolarization integral (PDI), or by measuring a physical activity such as acceleration using mechanical or electrical sensors. A profile or rate response function (RRF) is used to translate this physical parameter into a corresponding pacing parameter (such as, for example, pacing rate or pacing interval).

An important feature of existing rate response pacemakers of the type described above is that at any given instance, the optimal or hemodynamic operation, the pacing rate is dependent not only on the metabolic demand but also on the physical condition or fitness of the patient, which in turn is closely dependent in his or her lifestyle. Therefore, one of the parameters that must be programmed into the pacemaker when the pacemaker is initialized or reprogrammed is a parameter indicative of this physical condition. In its crudest form, this parameter may have three values: very fit, average, and unfit. This parameter must be determined by the clinician based on his experience with other patients, his physical examination of the patient, as well as information from the patient himself. To assist him in this determination, the clinician may ask the patient to exercise, i.e., walk, jog or climb steps, for a prescribed time period. The patient's endurance to the exercise (length of exercise) can also be used as an indicia of his condition. However, at best, at the end, the value entered by the clinician is an educated guess, and often may be inaccurate. Exercise testing is often too time consuming and prone to physiological factors.

A further problem is that as time goes by, the patient's lifestyle changes, i.e., he may become more, or less active, his physical fitness level changes accordingly. Usually, the change in lifestyle occurs gradually. However, even if this change is drastic, the physical fitness level changes relatively slowly. For optimal performance, the pacemaker parameters should be adjusted dynamically for changes in the physical fitness.

In any event, existing pacemakers are set normally for a certain fitness level, and if this level was set incorrectly in the first place, or because the physical fitness of the patient changed, the pacemaker will not generate the optimum response which will unnecessarily burden the patient's heart.

One patent that indirectly addresses this problem is U.S. Pat. No. 4,856,522 to Hansen in which the clinician sets a desired rate profile for converting minute volume to pacing rate and the metabolic demand sensor adapts over time by adjusting the relationship to meet this target profile. However, in this reference there is no suggestion for actually keeping track of the patient's physical condition, or for dynamically changing the rate profile set by the physician.

The present invention deals with the fundamental issue of what criteria should a pacemaker use to continuously modify the relationship between the metabolic demand parameter and the pacing parameter to take into consideration changes in the physical condition of the patient, or to automatically compensate for incorrect physical condition information. In the process of performing this function, the pacemaker automatically adjusts the patient's average and minimum pacing rates. In addition, by monitoring the relationship between the average value and the peak value of the metabolic demand parameter, the pacemaker is able to adjust the maximum allowable pacing rate.

OBJECTIVES AND SUMMARY OF THE INVENTION

In view of the above, it is an objective of the present invention to provide an implantable pacemaker which automatically and dynamically determines the true physical fitness of a patient.

A further objective is to provide a pacemaker which adjusts its rate response characteristics to suit the true fitness level of the patient.

A further objective is to provide a pacemaker which generates boundary conditions (i.e. minimum average rates) automatically to the physical fitness of a patient.

Briefly, a pacemaker constructed in accordance with this invention includes a sensor for sensing intrinsic cardiac events, a pacing pulse generator for generating pacing pulses on demand in accordance to commands from a state machine and a metabolic demand sensor. The intrinsic events are used in a fitness determination scheme to determine the physical fitness of the patient. The metabolic demand is translated then into a corresponding pacing parameter in accordance with the physical fitness of the patient.

DETAILED DESCRIPTION OF THE INVENTION

Figure 1:
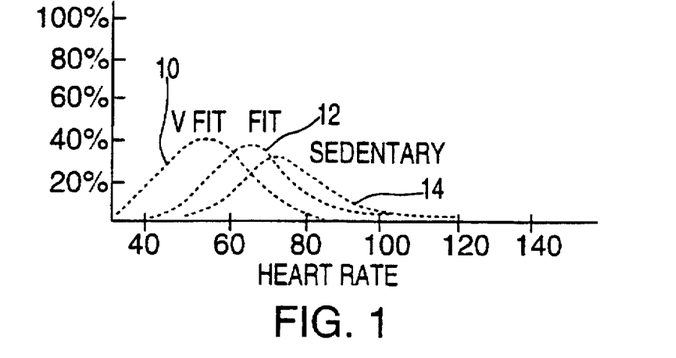
FIG. 1 shows typical heart rate distributions in percentiles for a very fit, an average fit and a sedentary person.

Referring now to FIG. 1, rate profiles 10, 12 and 14 indicate statistical data obtained from various cardiac patients. More specifically, profile 10 indicates in percentages the amount of time or frequency for heart rates from about 20 bpm to about 110 bpm for a physically very fit person. As seen in this Figure, the weighed average is about 55 bpm at a percentile level of about 45%. That is, during any given time duration in excess of a day or so, 45% of the time, the patient's heart beats in a range around 55 bpm, about 38% of the time it beats at around 60 bpm and so on.

For a person having an average physical fitness (profile 12) the weighed average is 40% at about 65 bpm. For a sedentary person (profile 14) the weight average is about 75 bpm at about 35%. It can be seen that as the fitness of a person increases, both the range and the average heart rate decreases. This effect is more dramatically shown in FIG. 2 by curves 16, 18 and 20, which represent the cumulative percentiles or integrals of profiles 10, 12 and 14, respectively. As can be seen from these latter curves, the cumulative rate curve shift to the left as a patient's physical condition improves. Moreover, each curve is easily characterized by the values at the 50% and about 90% level, the curve being monotonic in between.

Therefore, the actual physical fitness level of a patient can be characterized in a pacemaker by calculating the rates corresponding to certain preselected percentile levels. Accordingly, in the present pacemaker, the patient's activity is continuously monitored. The rate response function used for mapping the metabolic demand parameter into a corresponding metabolic indicated pacing parameter is then adjusted in accordance with the patient's physical fitness level. In this manner, the pacemaker can be adjusted to generate pacing pulses at the minimum heart rates that meet the patient's hemodynamic requirements.

It is known from standard literature, it takes about 40–60 days for a person's physical condition to compensate for a change in lifestyle. For example, one such change may consist of a patient who is initially sedentary and then starts exercising sufficiently and often enough so that his heart beat exceeds 50% of his peak rate at least three times a week, each exercising taking at least twenty minutes. As a result, at the end of about 50 days, his average heart rate and minimum decreases by about 10 bpm. For more intense exercise, the change in his physical fitness is even more rapid. As long as the patient retains this level of exercise, his average heart beat stays at this low level. If he increases the exercise level (i.e., duration, frequency, and/or intensity) his average heart rate decreases further. If he reduces his exercise level average, his heart rate slowly increases, and thus the benefits of exercise slowly decrease.

Figure 2:
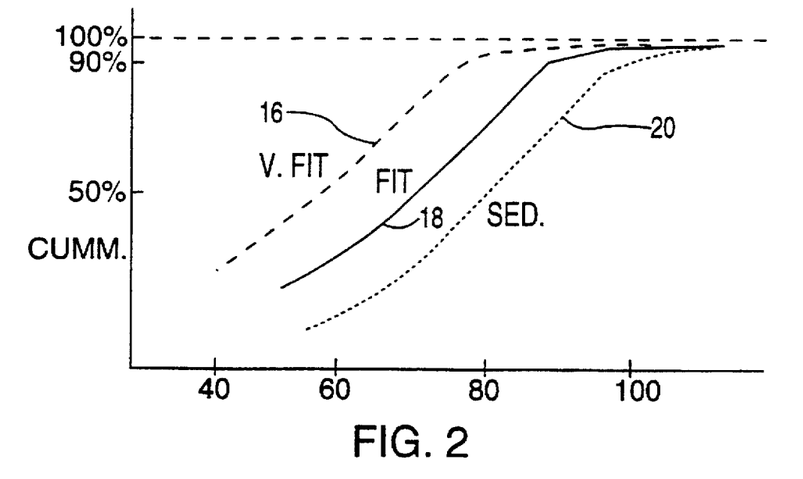
FIG. 2 shows the cumulative percentiles for the rate distributions of FIG. 1.

Thus, the cumulative heart beat curve of a person moves back and forth, between the curves 16 and 20 shown in FIG. 2, as in the course of a lifetime, a person changes his lifestyle and physical fitness level. This phenomenon is used in the present invention as described below.

FIG. 2 is a convenient way to present the concept of patient fitness. The curves 16, 18, 20 are idealized to a certain extent. However, they are used to illustrate the following observations.

(1) As the patient becomes fitter they spend more time at lower rates;

(2) An arbitrary point near the maximum rate such as 92% mark represents different rates, slower for fitter patients;

(3) The average rate decreases; this is the rate below which patients spend 50% of their time;

(4) The minimum rate (the 10% demarcation), also decreases.

Any percentile mark on FIG. 2 may be used to generate a continuous physical fitness indicia. For example the indicia for the 92% percentile mark is shown in FIG. 2a.

Figure 2A:
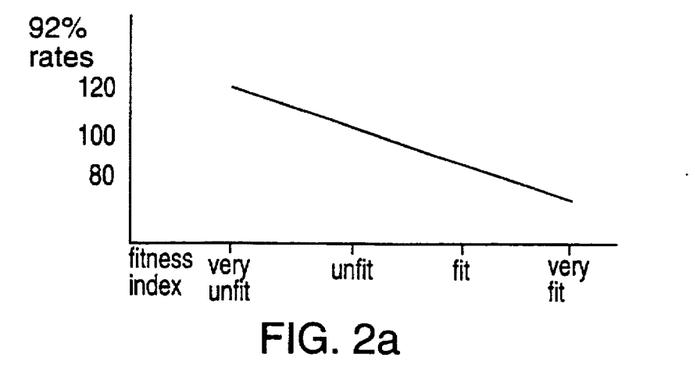
FIG. 2a shows how a particular percentile mark (92%) may be used to generate a physical fitness indicia.

A similar diagram to FIG. 2a could be drawn for the average (50% percentile) or minimum (10% percentile) rates. These derived values from the life style of the patient can be used in an adaptive algorithm, which over time generates an appropriate relationship between MV and pacing rate.

Figure 3:
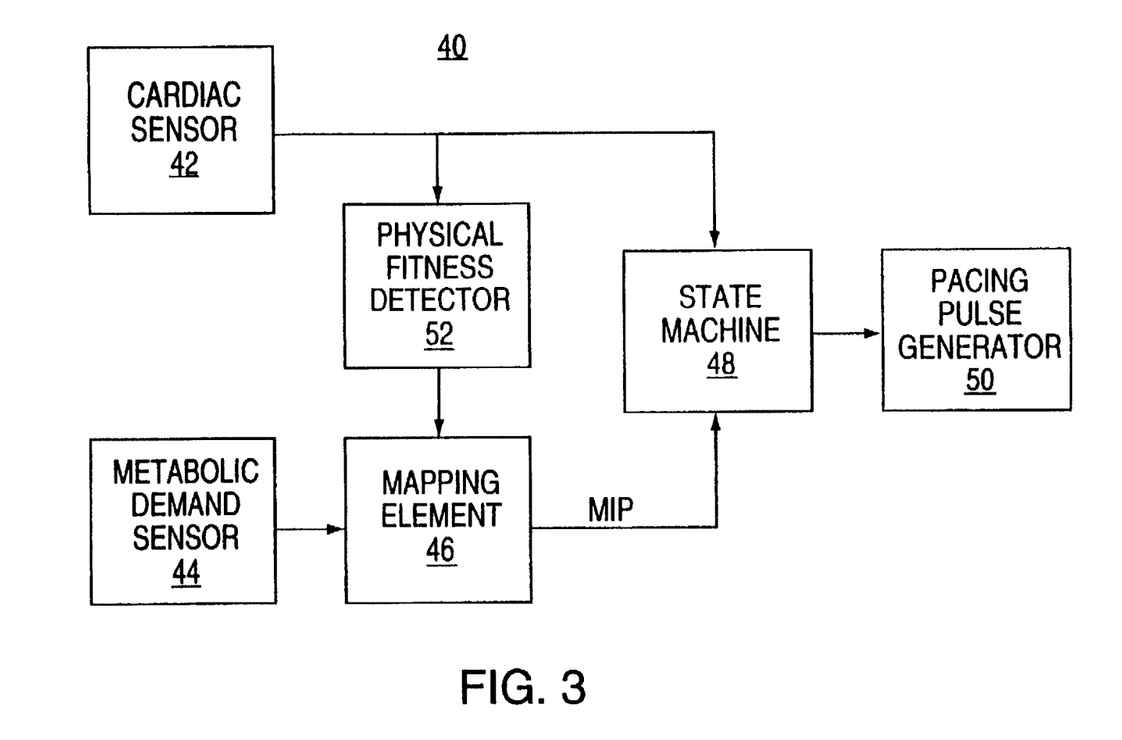
FIG. 3 shows a block diagram of a pacemaker constructed in accordance with this invention.

Referring to FIG. 3, a pacemaker 40 constructed in accordance with this invention includes a cardiac sensor 42 for receiving signals from the patient's heart indicative of intrinsic cardiac activity. (As is apparent to a person skilled in the art, typically pacemaker 40 may be a dual chamber pacemaker which senses and/or paces one or both chambers of the patient's heart. However, a single chamber pacemaker is described herein for the sake of simplicity). The pacemaker 40 further includes a metabolic demand sensor 44 for sensing the hemodynamic needs of the patient's body. As mentioned above, this sensor 44 could be based on physiological parameters (such as minute volute, QT interval, PDI, etc.) or a mechanical sensor which actually measures a physical activity parameter such as acceleration.

In any event, the output of the sensor 44 is fed to a mapping element 46 which uses an RRF function to convert the metabolic demand from sensor 44 into a corresponding metabolic indicated parameter (MIP). The output of sensor 42 (indicative of intrinsic cardiac activity) and the metabolic indicated parameter are both fed to a state machine 48. The state machine 48 uses these parameters and a set of preprogrammed rules to generate (when required) pacing commands for pacing generator 50. The pacing generator 50 in response generates pacing pulses which are sent to the patient's heart via appropriate electrodes (not shown). The rules in the state machine 48 set the various pacing parameters such as AV delays, blanking periods, post ventricular atrial refractory periods, and other parameters associated with single and dual chamber pacing as described in U.S. Pat. No. 5,441,523.

Importantly, in accordance with the present invention pacemaker 40 is also provided with a physical fitness detector 52 which also receives at least some of the events detected by the cardiac sensor 42, and generates an indicia of the current physical fitness of the patient. Detector 52 provides this information to the mapping element 46 which in response selects the appropriate RRF mapping function.

It should be understood that the physical fitness detector 52, mapping element 46, and state machine 48 may all be implemented on a single microprocessor but are shown here for convenience as discreet elements.

Figure 4:
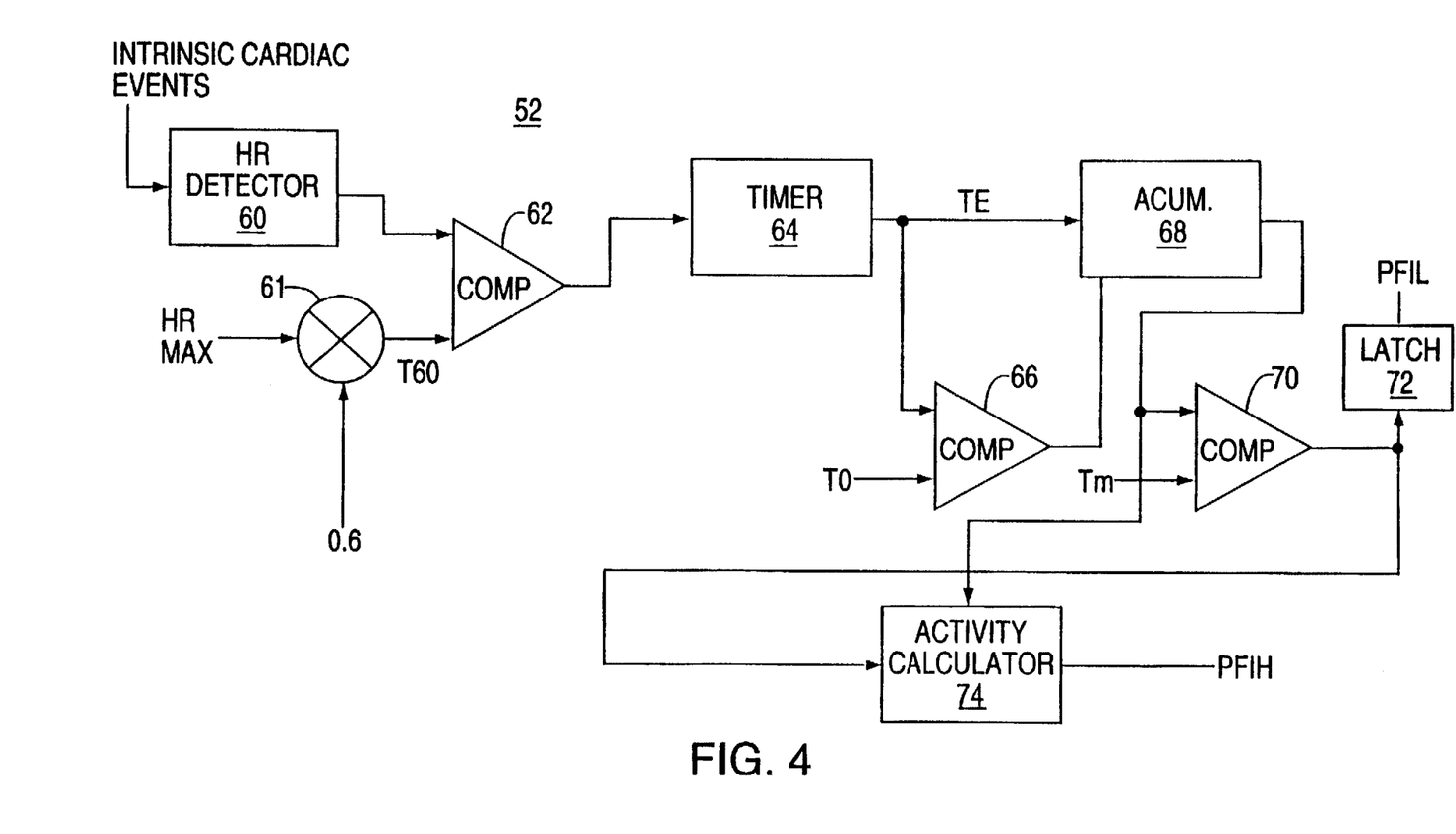
FIG. 4 shows a block diagram for the physical fitness detector for the pacemaker of FIG. 3.

More particularly, heart beats are logged by the detector 60. The detector 60 collects either all, or a sampling of the heart rates over a long time period, such as for example, over the last 30–40 days, and preferably over the last 35 days.

As shown in FIG. 4, the physical fitness detector 52 includes a heart rate detector 60 which receives the intrinsic cardiac events from sensor 42 and generates a numerical value for the current detected heart rate (HR) of the patient. In addition, the current maximum allowable heart rate (HRMAX) for the patient (this is normally a programmable variable) is also fed to a multiplier 62 where it is multiplied by 0.6 to obtain a 60% threshold value T60.

Figure 5:
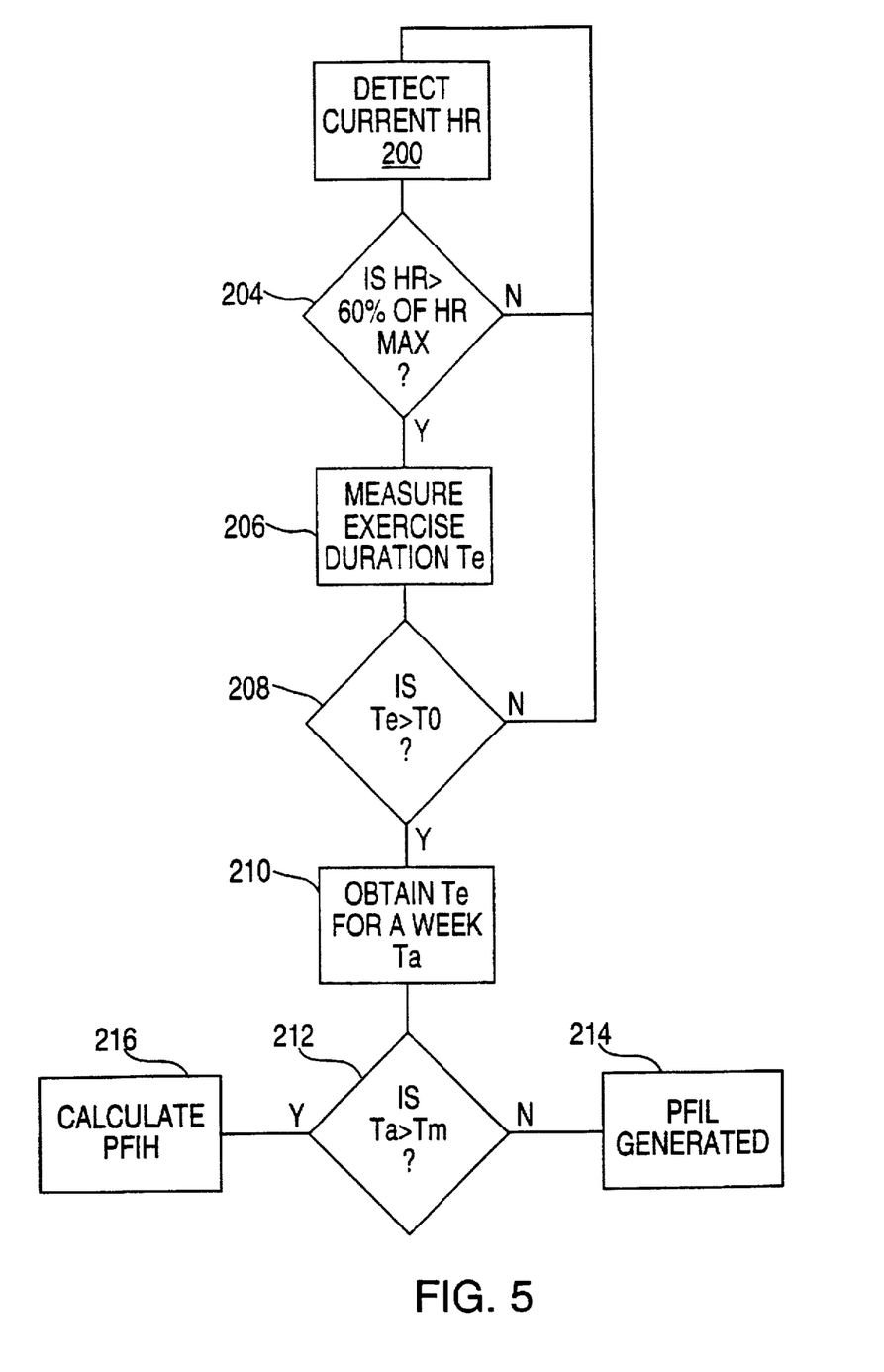
FIG. 5 shows a flow chart for deriving a physical fitness criteria.

The operation of the detector 52 is explained in conjunction with the flowchart of FIG. 5.

In Step 200 detector 60 detects heart rate HR.

The output of detector 60 and the T60 value are fed to a comparator 62 which generates an output if the current rate HR is higher. The comparator 62 in effect is used to determine the onset of exercise by the patient (Step 204). The purpose of this test is to insure that the patient is involved in an exercise which has a sufficiently high intensity, and is not merely transitory. The output of comparator 62 remains high as long as the patient continues exercising. This output is used to trigger a timer 64 used to measure the duration of the exercise Te (Step 206). This duration Te is fed concurrently to a comparator 66 and an accumulator 68. Comparator 66 compares Te to a threshold value TO to determine if the exercise has been maintained long enough to have any meaningful effect on the physical fitness of the patient. Te may be, for example, twenty minutes. If Te exceeds this limit, then the accumulator 68 takes it into consideration. Otherwise, Te is ignored (Step 208). In most cases there will be a scaling factor such that less than 20 min. will be considered.

Accumulator 68 maintains a running sum of the total amount Ta of all the exercising sessions for a given time period (for example, a week) which have met the criteria set by comparator 66 (Step 210). In Step 212, a comparator 70 compares the total amount Ta to a threshold level Tm. A low Ta indicates that the patient has not exercised enough and therefore his physical condition is deteriorating. Under these conditions in Step 214, a signal PFIL is generated by a latch 12 to indicate a low physical fitness indicia.

If the output of the comparator is high, i.e., Ta>Tm, then an activity calculator 74 is used to calculate the total amount of time Tn spent above a threshold level T1 which may or may not be the same as Tm. The difference between these signals is indicated by a signal PFIH (high physical condition Indicia) (Step 216).

Figure 6:
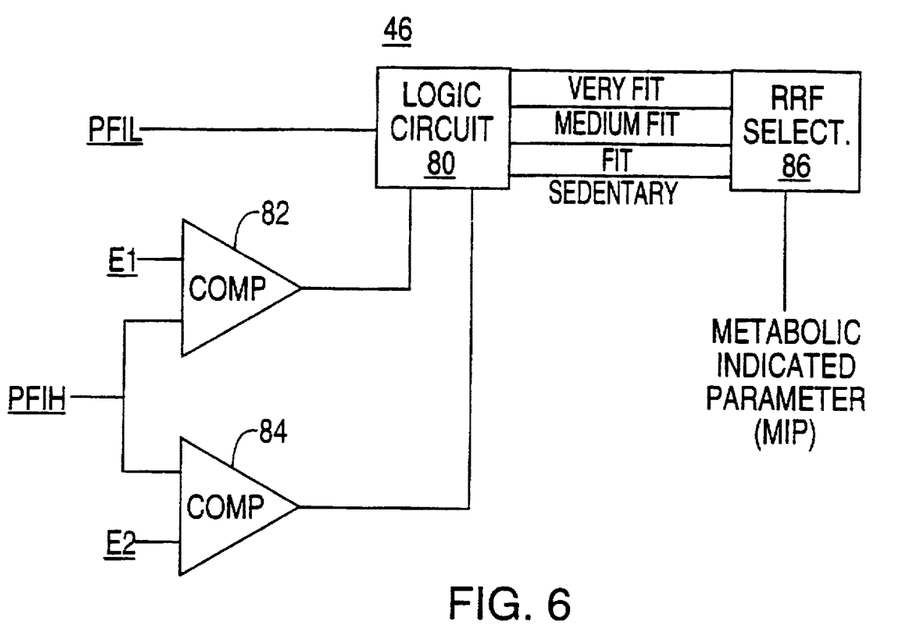
FIG. 6 shows details of mapping element of FIG. 3.

FIG. 6 shows details of the mapping element 46. The mapping element 46 receives the signals PFIL and PFIH. The element 46 includes a logic circuit 80 and two comparators 82 and 84. Comparators 82 and 84 are used to determine if the signal PFIH and hence the total amount of exercise by the patient, is in between a range between E1 and E2. The comparator 82 generates an output if the indicia PFIH is above level E1. Comparator 84 generates an output if the indicia PFIH is above level E2.

In response, the logic circuit generates one of four outputs, depending on its inputs. If the inputs indicate that the patient has a 'normal' fitness level, i.e., none of the inputs are high, then the logic circuit generates a FIT output indicating a normal level of fitness. For a low fitness level from input PFIL, the logic circuit generates a low or 'sedentary' output. If only comparator 82 generates an output, logic circuit 80 generates a 'MEDIUM FIT' output indicating that the patient has a medium fitness, i.e., a fitness somewhat higher than normal FIT level.

Finally, an input from comparator 84 indicates a high fitness level and in response, the logic circuit 80 generates a 'VERY FIT' output. These inputs are use by the RRF selector 86 to generate an appropriate RRF mapping profile as described below.

In the above description four levels of fitness are described, as an exemplary embodiment, it being understood that the concepts presented herein may be expanded to any number of such levels, as desired.

Referring first back to FIG. 2, as discussed above, a person having an average fitness level is characterized by the cumulative curve 18, a very fit person may be characterized in comparison by cumulative curve 16, and a sedentary person may be characterized by curve 20.

As indicated by these curves, the following parameters are generally applicable to various patients:

| | RATES (BPM) | | |
|---|---|---|---|
| | POOR FITNESS | NORMAL FITNESS | HIGH FITNESS |
| CUM. 92% | 120 | 100 | 85 |
| CUM. AVR. (50%) | 85 | 75 | 60 |
| CUM. MIN (10%) | 70 | 60 | 50 |

The 92% level is a useful criteria because it corresponds to moderate exercise level that is reached typically by a person at least once a day.

A person having a medium fitness level is characterized by heart rates falling somewhere between the normal (or FIT) and very fit characteristics.

Using the numbers in the table above the boundary conditions for computing new RRF values can proceed as in the Hansen U.S. Pat. No. 4,856,522.

Figure 8:
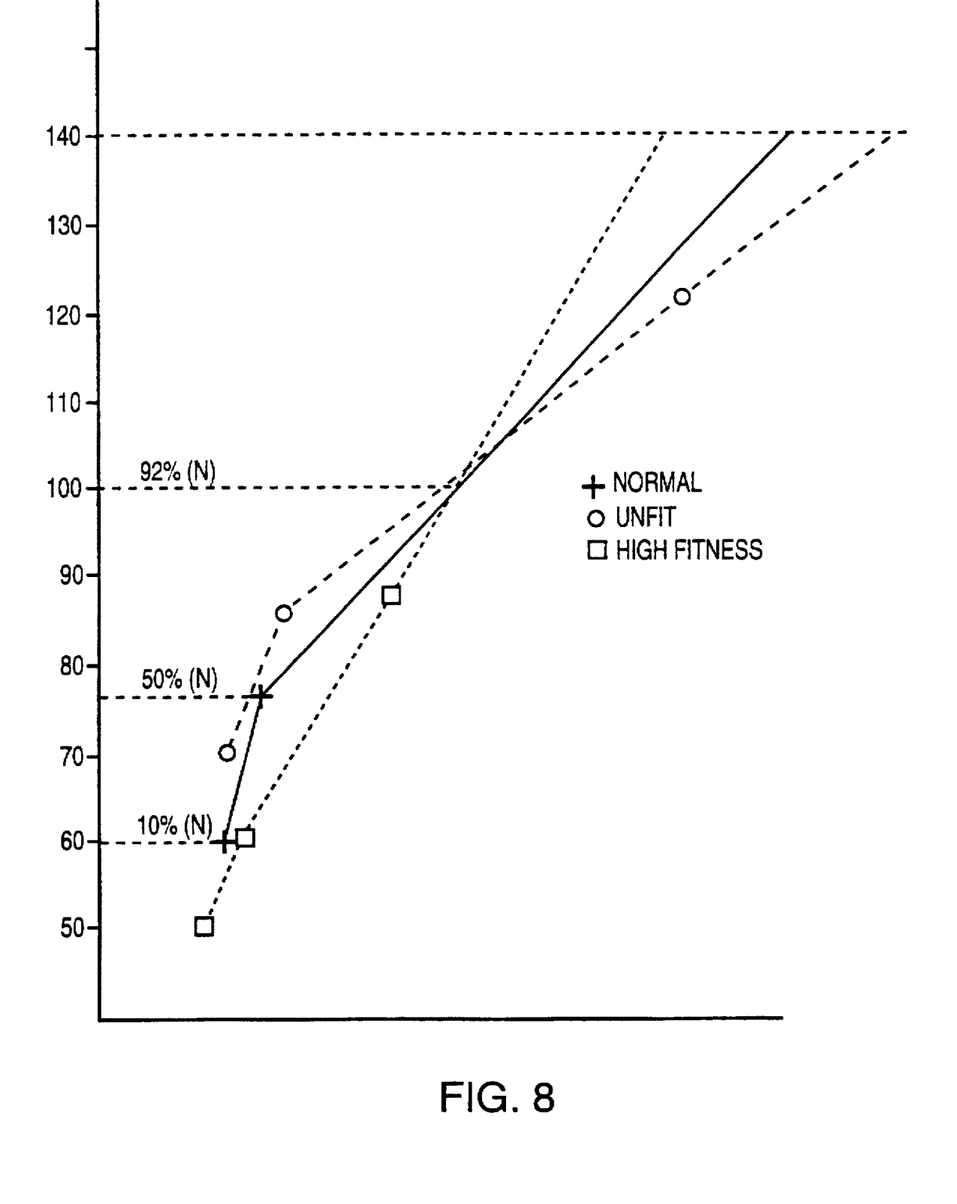
FIG. 8 shows a family of RRF curves.

In the present invention, it is contemplated that the techniques describe in the above-mentioned Patent are used to generate first the minimum, average and a 92% cumulative values for the metabolic demand parameters, i.e., MV_MIN, MV_AVR, and MV_92. For a person having a normal fitness level, these parameters may then be used to generate a profile 100 as shown in FIG. 8. In this Figure, profile 100 is shown as being defined by two line segments. One skilled in the art will appreciate that other profiles may be defined in a similar manner which may have an exponential or other (preferably) monotonic shape.

Assuming that for a given patient, the output from logic circuit 80 shows a normal fitness level, the RRF selector 86 selects profile 100, and using this profile, for every instantaneous MV parameter, an appropriate metabolic indicated parameter is generated. In FIG. 3, this MIP is fed to the state machine 48, as discussed.

Figure 7:
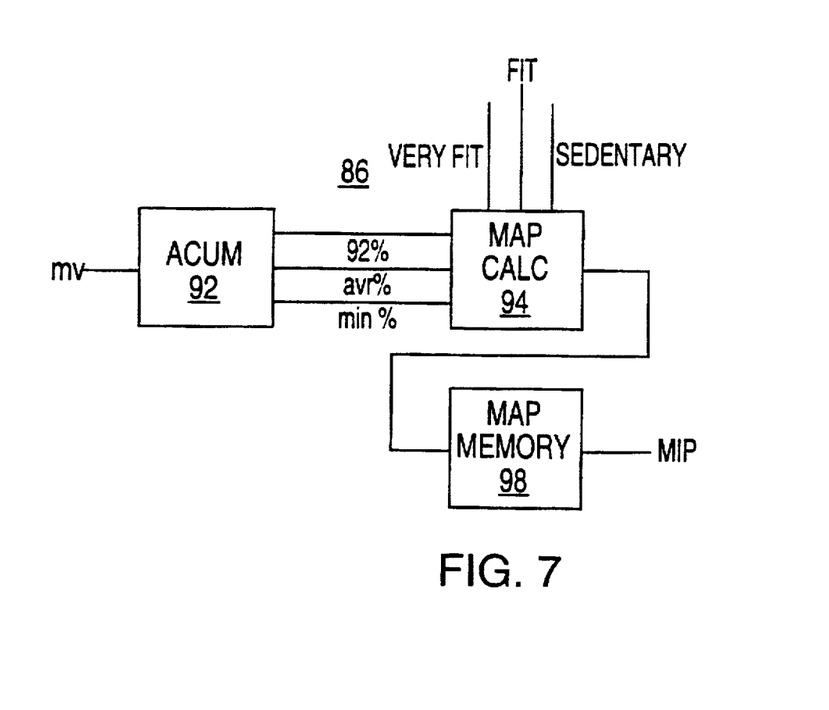
FIG. 7 shows a block diagram for the RRF mapping circuit of FIG. 6.

Referring to FIG. 7, the RRF selector 86 includes an accumulator 92 which monitors the parameter DMV and generates a cumulative histogram which defines several critical values for the cumulative minute volume, such as MV_MIN, MV_AVR and MV_92. The corresponding cumulative MIR values are known form the above table, and therefore the profile 100 is calculated by calculator 94. Preferably the calculator 94 is implemented as a look-up table.

The present invention contemplates monitoring the person's exercise level on a long term basis, i.e. 35 days, and based on this monitoring develops indicia about whether the person's fitness level has changed or not.

Assume that after several months, the life style of the patient changes resulting in his level of fitness changing from 'normal' to 'very fit' as indicated by the output of the logic circuit 80. In response, map calculator 94 generates now profile 102, shown in FIG. 8, using the MV percentiles from the accumulator 92 and the MIR values from the above table. As compared to curve 100, curve 102 may be viewed as being shifted to the right.

Assume now that instead of becoming more fit, the patient becomes less fit, and that this new condition is indicated by logic circuit 80 as sedentary. Once again, the calculator 94 generates a new profile 104 based on the new MV values from accumulator 92 and the MIR values from the above table. As seen in FIG. 8, this new profile may be viewed as shifting the profile 100 slightly to the left.

Importantly, it should be appreciated that at least initially the MV values corresponding to the 10%, 50% and/or 92% percentiles of MIR are not known but are derived dynamically within the pacemaker over time.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable pacemaker comprising:
   a sensor for sensing intrinsic events in a patient's heart, and generating sensed cardiac signals;
   a pace generator for generating pacing signals in response to commands;
   a metabolic sensor for sensing a metabolic demand of a patient and generating in response a metabolic demand signal;
   a physical fitness determinator for sensing a long term physical fitness of said patient and generating in response a physical fitness indicator; and
   a controller receiving said sensed cardiac signals, said metabolic demand signal and said physical fitness indicator and generating in response said commands.

2. The pacemaker of claim 1 wherein said metabolic sensor senses a physiological characteristic of the patient.

3. The pacemaker of claim 2 wherein said physiological characteristic is one of a minute volume, a QT interval and a PDI.

4. The pacemaker of claim 1 wherein said metabolic sensor senses a physical activity using a mechanical sensor.

5. The pacemaker of claim 4 wherein said mechanical sensor is an accelerometer.

6. An implantable pacemaker comprising:
   a cardiac sensor for sensing intrinsic cardiac activity;
   a pacing generator for generating pacing signals in accordance with said intrinsic cardiac activity;
   an activity sensor for sensing physical activity by said patient over a prolonged time period;
   a memory for collecting a total exercise duration during said prolonged time period; and
   output for generating from said memory a physical fitness indicia for said patient.

7. The pacemaker of claim 6 further comprising a controller for generating commands for said pacing generator in accordance with said intrinsic cardiac activity and said physical fitness indicia.

8. The pacemaker of claim 6 wherein said activity sensor includes a metabolic demand sensor for sensing a metabolic demand.

9. The pacemaker of claim 8 wherein said metabolic demand sensor senses a physiological characteristic.

10. The pacemaker of claim 8 wherein said physiological characteristic is one of a minute volume, PDI or QT interval.

11. The pacemaker of claim 8 wherein said metabolic demand sensor is a mechanical sensor for sensing a physical characteristic associated with the patient's body.

12. The pacemaker of claim 11 wherein said mechanical sensor is an accelerometer.

13. A rate responsive implantable pacemaker for pacing a patient in an optimized hemodynamic mode, said pacemaker comprising:
   a cardiac sensor for sensing intrinsic cardiac activity in a cardiac chamber and generating a sensed signal;
   a pacing pulse generator for generating pacing pulses to the patient's heart in response to pacing commands;
   a physical fitness monitor for monitoring the actual physical fitness of the patient, said monitor generating a physical fitness indicia;
   an activity sensor sensing physical activity of the patient and generating in response a metabolic demand parameter;
   a mapping member for mapping said metabolic demand parameter into a metabolic indicated parameter in accordance with a preselected profile; and
   a controller for generating said pacing commands in accordance with said sensed signal, said physical fitness indicia and said metabolic demand parameter.

14. The pacemaker of claim 13 further comprising an adjusting circuit for adjusting said preselected profile in accordance with said physical fitness indicia.

15. The pacemaker of claim 13 wherein said physical fitness monitor includes an exercise sensor for sensing an exercise period of said patient and an accumulator for accumulating the durations of the exercise periods during a preselected duration.

16. The pacemaker of claim 15 wherein said accumulator is constructed and arranged to accumulate said durations for a period of 30–40 days.

17. The pacemaker of claim 15 wherein said physical fitness monitor further includes a threshold determinator to determine an intensity of exercise during each exercise period, said accumulator accumulating only exercise periods having a preselected intensity.

18. The pacemaker of claim 13 wherein said physical fitness monitor derives signals indicative of very fit, normally fit and sedentary patients.

* * * * *